US006245561B1

(12) United States Patent
Knight et al.

(10) Patent No.: US 6,245,561 B1
(45) Date of Patent: Jun. 12, 2001

(54) β-ALETHINE USE IN CELL CULTURE AND THERAPY

(75) Inventors: Galen D. Knight; Paul L. Mann; Terence J. Scallen, all of Albuquerque, NM (US)

(73) Assignee: University of New Mexico

( * ) Notice: Subject to any disclaimer, the term of this patent is extended or adjusted under 35 U.S.C. 154(b) by 0 days.

(21) Appl. No.: 08/346,177

(22) Filed: Nov. 22, 1994

Related U.S. Application Data

(60) Division of application No. 07/919,253, filed on Jul. 27, 1992, now abandoned, which is a continuation-in-part of application No. 07/549,104, filed on Jul. 6, 1990, now abandoned.

(51) Int. Cl.[7] .............................. C12N 5/00; C12N 5/08; C12N 5/02
(52) U.S. Cl. ......................... 435/325; 435/1.1; 435/374; 435/375; 435/377; 435/383; 435/384; 435/405; 435/2
(58) Field of Search .............................. 435/1.1, 2, 240.1, 435/240.2, 240.21, 240.23, 240.25, 240.26, 240.3, 240.31, 325, 374, 375, 377, 383, 384, 405; 564/154; 514/626

(56) References Cited

U.S. PATENT DOCUMENTS

| 2,835,704 | 5/1958 | Walton | 260/562 |
|---|---|---|---|
| 4,552,765 | 11/1985 | Mita et al. | 514/513 |
| 4,927,762 | * 5/1990 | Darfler et al. | 435/240.31 |
| 5,013,546 | 5/1991 | Gottlieb et al. | 424/85.1 |

FOREIGN PATENT DOCUMENTS

| WO 85/00167 | 1/1985 | (WO) . |
|---|---|---|
| WO 92/00960 | 1/1992 | (WO) . |

OTHER PUBLICATIONS

Oiry et al, "Synthesis and Radioprotective Activity of New Cysteamine and Cystamine Derivatives", J. Med. Chem. 29(11):2217–2225 (1986).
Komoriya et al, "Anti–Arthritic and Immunoregulatory Effects of TI–31 on Collagen–Induced Arthritis", Japan J. Pharmacol. 45:389–396 (1987).
Komoriya et al, "Inhibitory effect of TI–31 on autoimmune nephritis in B/NZW $F_1$ mice through regulation of the immune response", Immunopharmacology 13:89–98 (1987).
"Current Protocols in Immunology", Ed. Coligan et al., Greene Publishing Assoc. and Wiley–Interscience, pp. 4.2, 4.2.4, 4.3.1, 7.0.5, 7.0.7, 1991.*
Rheinwald, "Chapter 5", from: "Cell Growth and Division, a New Practical Approach", Ed. R. Baserga, IRL Press, pp. 81–94, 1989.*
Lange, "Chapter 4" From: "Cell Growth and Division, a Practical Approach", Ed. R. Baserga, IRL Press, pp. 81–94, 1989.*
Waldmann, "Monoclonal Antibodies in Diagnosis and Therapy", Science 252:1657–1662 (1991).
Roederer et al, "Cytokine–stimulated human immunodeficiency virus replication is inhibited by N–acetyl–L–cysteine", Proc. Natl. Acad. Sci. USA 87:4884–4888 (1990).
Foon, "Biological Response Modifiers: The New Immunotherapy", Cancer Research 49:1621–1639 (1989).
Osband et al, "Problems in the investigational study and clinical use of cancer immunotherapy", Immunology Today 11(6):193–195 (1990).
Immunology Second Edition, edited by Jean–Francois Bach, M.D., D.Sc., pp. 88–105.
Stalb et al, "Protection against Experimental Cerebral Metastases of Murine Melanoma B16 by Active Immunization", Cancer Research 53:1113–1121 (1993).
Sachs, "Growth, Differentiation and the Reversal of Malignancy", Scientific American, pp. 40–47 (1986).
Cockroft, "Nutrient requirements of rat embryos undergoing organogenesis in vitro", J. Reprod. Fert. 57:505–510 (1979).
Droge et al, "Modulation of Lymphocyte Functions and Immune Responses by Cysteine and Cysteine Derivatives", The American Journal of Medicine 91(suppl 3C):3C–140S (1991).

* cited by examiner

*Primary Examiner*—Ronald B. Schwadron
(74) *Attorney, Agent, or Firm*—Judith A. Evans

(57) ABSTRACT

β-alethine is employed in the differentiation, phenotypic expression, and vitalization of cells, for both in vivo and in vitro applications. Particular applications include the use of β-alethine in the treatment of immune disorders and diseases, and in the promotion of cell cultures.

11 Claims, 11 Drawing Sheets

THE EFFECT OF BETA-ALETHINE ON DIFFERENTIATION
HUMAN LEUKOCYTES

BETA-ALETHINE VS. MURINE NS-1 MYELOMA

β-ALETHINE USE IN CELL CULTURE AND THERAPY

This is a division of application Ser. No. 07/919,253, filed Jul. 27, 1992, now abandoned, which is a continuation-in-part of application Ser. No. 07/549,104, filed Jul. 6, 1990, now abandoned.

BACKGROUND OF THE INVENTION

1. Field of the Invention

The invention relates to the use of β-alethine and/or its corresponding monosulfide, β-alethine, for the inducement of cell differentiation, adaptation of cells to culture, and enhancement of cell phenotypic expression, vitality, longevity, and production. In particular, the invention relates to the use of β-alethine for inducing the differentiation of precursor cells into specialized cells, for normalizing function of malfunctioning cells, and for eliminating intractable cells (cells which are "resistant to cure, relief, or control", Dorland's Illustrated Medical Dictionary, 26th Edition, 1974, W. B. Saunders, Philadelphia, Pa., U.S.A.).

Cellular differentiation is a well-known phenomenon which broadly refers to processes by which precursor cells (commonly termed "stem cells") develop into specialized cells. Differentiation compounds, i.e., those factors which induce cell multiplication, in the literature (see, e.g., "Growth, Differentiation, and the Reversal of Malignancy", Scientific American, pp. 40–47, January, 1986, and the publications cited therein) and the implications of each with respect to therapeutic use in the treatment of disease or disorders of the body are of much current interest. The present application relates to the identification of β-alethine as a non-cell-lineage-dependent differentiation compound, and the use of β-alethine to induce differentiation and/or normalization of the function of a variety of cells, particularly for therapeutic benefits.

"Phenotypic cell expression" is defined herein as the manifestation of an entire range of physical, biochemical, and physiological characteristics of an individual cell as determined both genetically and environmentally, in contrast to "genotypic cell expression", which in the art solely refers to the expression of the cell chromosomal sequence. [See, for example, Dorland's Illustrated Medical Dictionary, 26th Edition, 1974, W. B. Saunders, Philadelphia.] Biological activity of the compounds of the invention thus includes modulation of the expression of genetic material of cells in culture as influenced by the condition and environment of each cell, including the age of the cell, the culture or conditions employed, and the presence of optionally added biological effectors.

2. Discussion of Related Art

β-alethine is an endogenous thiol known to be produced in vivo as a byproduct of metabolic pathways. It is related via these pathways to pantothenic acid, which is a vitamin having known nutritional benefits (see, e.g., J. Reprod. Fert. 57: 505–510 [1979]), and related compounds have been suggested for use in conjunction with radiotherapy as radio-protectors (J. Med. Chem. 29: 2217–2225, 1986; WO 85/00157, Jan. 17, 1985). No other relevant asserted biological functions of this compound are known to be described in the prior art. The compound is primarily well-known as a starting material for the chemical synthesis of related compounds (see, e.g., Japanese patent applications (83) 198461; (83) 46063A2; (81) 156256A2; (81) 104861A2; (80) 124755; (75) 62932; (80) 07222; and U.S. Pat. Nos. 2,835,704 and 4,552,765; for examples of the preparation of β-alethine, β-alethine, pantetheine, and its derivatives or intermediates, and also for Coenzyme A and Coenzyme A derivatives or intermediates).

It is well-known that endogenous thiols and disulfides are critical to the function of a multitude of thiol- and disulfide-dependent branch-point enzymes controlling access to major metabolic pathways. Glutathione (GSH, gamma-glutamyl cysteinylglycine, an acid tripeptide thiol) is the most abundant thiol in mammalian cells, and an entire regulatory and regenerating system ensures an adequate supply of this reducing agent (3,4,5), which maintains and buffers cell thiol/disulfide ratios. Coenzyme A (CoA) and lipoic acid are prevalent in mammalian systems and also regulate dependent enzyme activity. Xenobiotic thiols such as dithiothreitol (DTT, Cleland's reagent) or dithioerythritol are routinely used experimentally to regulate activity of thiol-dependent enzymes.

In response to demand, thiols such as GSH, CoA, and lipoic acid can, for example, activate thiol-activatable enzyme by reducing inactive oxidized (disulfide) enzyme to the corresponding thiol with a concomitant oxidation of the activating thiol to its corresponding disulfide (GSSG in the case of glutathione-GSH) according to the following scheme, wherein P is protein:

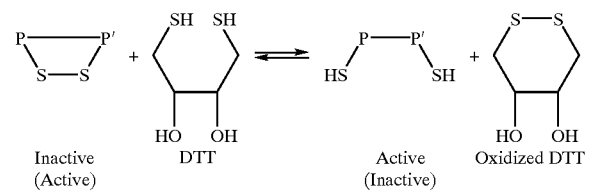

Inactive (Active)    DTT    Active (Inactive)    Oxidized DTT

Activity of thiol-dependent enzymes is a function of the availability of the thiols involved as expressed by the thiol/disulfide ratios of their thiol/disulfide redox buffers (upper arrow); interaction is complex, however, and activity is further dependent on additional factors such as substrate, ambient ions, and type of reducing thiol (membrane-bound enzymes, for example, are resistant to reduction by glutathione). Similarly, activity of disulfide-dependent enzymes (in parenthesis) is a function of the availability of disulfides, as expressed by the thiol/disulfide ratios of their redox pairs (lower arrow).

By the above mechanisms, endogenous thiol/disulfide redox buffers such as GSH/GSSG systems control the activity of many critical enzymes; thyroxine monodeiodinase is exemplary of thiol-dependent enzymes. Regulation of the activity of this enzyme by thiol/disulfide buffer controls the induction of a host of important enzymes, including HMG-CoA reductase, the branch-point enzyme for the isoprenoid pathway, which in turn regulates the production of essential isoprenoids such as steroid hormones, dolichol, cholesterol, and ubiquinone and the isoprenylation of proteins (6,7,8,9, 10,11). Glycolysis is also controlled by thiol-dependent and disulfide-dependent enzyme systems; phosphofructokinase, for example, is inactivated by disulfides, whereas fructose-1,6-bis-phosphatase with the reverse enzyme activity is activated by certain disulfides. Thiol-dependent enzymes also directly and/or indirectly control isoprenoid and oligosaccharide biosynthesis and the synthesis and utilization of thyroid hormones.

One mechanism postulated to participate in the in vivo regulation of thiol/disulfide equilibria is the oxidation of thiol to disulfide catalyzed by microsomal flavin-containing mixed function monooxygenase (herein referred to as "monooxygenase"). This monooxygenase catalyzes, for example, the oxidation of cysteamine to its corresponding disulfide, cystamine. A comparable oxygenase activity thus appears to be critical to the regulation of at least some thiol- and disulfide-dependent enzymes in vivo.

Certain other thiols (glutathione or cysteine or N-acetyl-cysteine) have been demonstrated in vivo to inhibit neoplasia (*Am. J. Med.* 91(3C): 122S–130S, 1991); to inhibit replication of HIV in cell cultures (*Proc. Natl. Acad. Sci. USA* 87 (12): 4884–8, 1990); to be markedly elevated in preneoplastic/neoplastic hepatocytes (*Mol. Carcin.* 2 (3): 144–9, 1989); to influence the proliferation of human peripheral blood lymphocytes (HPBL) and T-cells (*Am. J. Med.* 91(3C): 140S–144S, 1991) to reverse inhibition of lymphocyte DNA synthesis by glutamate in cells from HIV-infected patients (*Int. Immunol.* 1(4): 367–72, 1989); to reduce infectivity of herpes virus in vitro (*Acta. Virol. Praha.* 11(6): 559–61, 1967); to suppress HIV expression in monocytes (*Proc. Natl. Acad. Sci.* 88: 986–990, 1991); and to be systemically deficient in HIV-infected individuals (*Biol. Chem. Hoppe Seyler* 370: 101–08, 1989 and *The Lancet ii:* 1294–97, 1989). Regulation of HMG-CoA reductase activity by thiols and disulfides is well-known; as noted above, thyroxine monodeiodinase is a thiol-dependent enzyme, and this enzyme controls the induction of HMG-CoA reductase (*Eur. J. Biochem.* 4: 273–278, 1968). Hypercholesteremia and atherosclerosis, leading factors in heart disease, are now clearly linked to HMG-CoA reductase activity, and treatment of these conditions with various regulators of HMG-CoA reductase is known. HMG-CoA reductase activity is also linked to neoplasia, most recently by evidence of its role in the transformation of cells by activation of Ras protein which regulates oncogene expression (*Adv. Enzymol.* 38: 373–412, 1973; *Biochem. Soc. Trans.* 17: 875–876, 1989; *Science* 245: 379–385, 1989; *3-Hydroxy-3-Methylglutaryl Coenzyme A Reductase,* Sabine ed. CRC Press, Inc., Boca Raton, Fla., U.S.A., pp. 245–257, 1983).

SUMMARY OF THE INVENTION

The invention accordingly provides methods for inducing cell differentiation and normalization of cell function, and for enhancing cell phenotypic expression, vitality, longevity, and production employing β-alethine as differentiation compound. The invention has particular application in the differentiation of mammalian cells, including human cells, both in vitro and in vivo, most especially for normalizing cell development with respect to both cell maturation and differentiation-dependent cell growth; however, the use of β-alethine as differentiation compound for other cells, such as reptilian, avian, plant, insect, arachnid, rickettsial, bacterial, yeast, mold, protozoan, and fungus cells is also contemplated. Exemplary applications include the following: normalization of immunodeficient and autoimmune cell function (including the therapeutic use of β-alethine in the treatment of immunodeficiency and autoimmune diseases and disorders, particularly in mammals, and especially in humans); delay of cell senescence (including the therapeutic use of β-alethine in the treatment of diseases or disorders characterized by presenescent or prematurely senescing cells, particularly in mammals, and especially in humans); enhancement of cellular phenotypic expression, production, and vitality, and the therapeutic benefits derived therefrom; and adaptation of resistant cells to culture and the diagnostic and therapeutic uses derived therefrom. Within the scope of the present invention, β-alethine, the reduced form of β-alethine, is to be considered the biological equivalent of β-alethine for purposes of practicing the invention, as β-alethine is readily reduced to β-alethine in vivo, for example by abundant intracellular thiol compounds and enzymes, such as glutathione and thiol-disulfide isomerases in mammals. Both compounds have the advantage of having inherent antioxidative properties; however, β-alethine is chemically more resistant to autoxidation than β-alethine, and the use of β-alethine in the present invention is generally preferred for this reason.

DETAILED DESCRIPTION OF THE INVENTION

Figure 1:
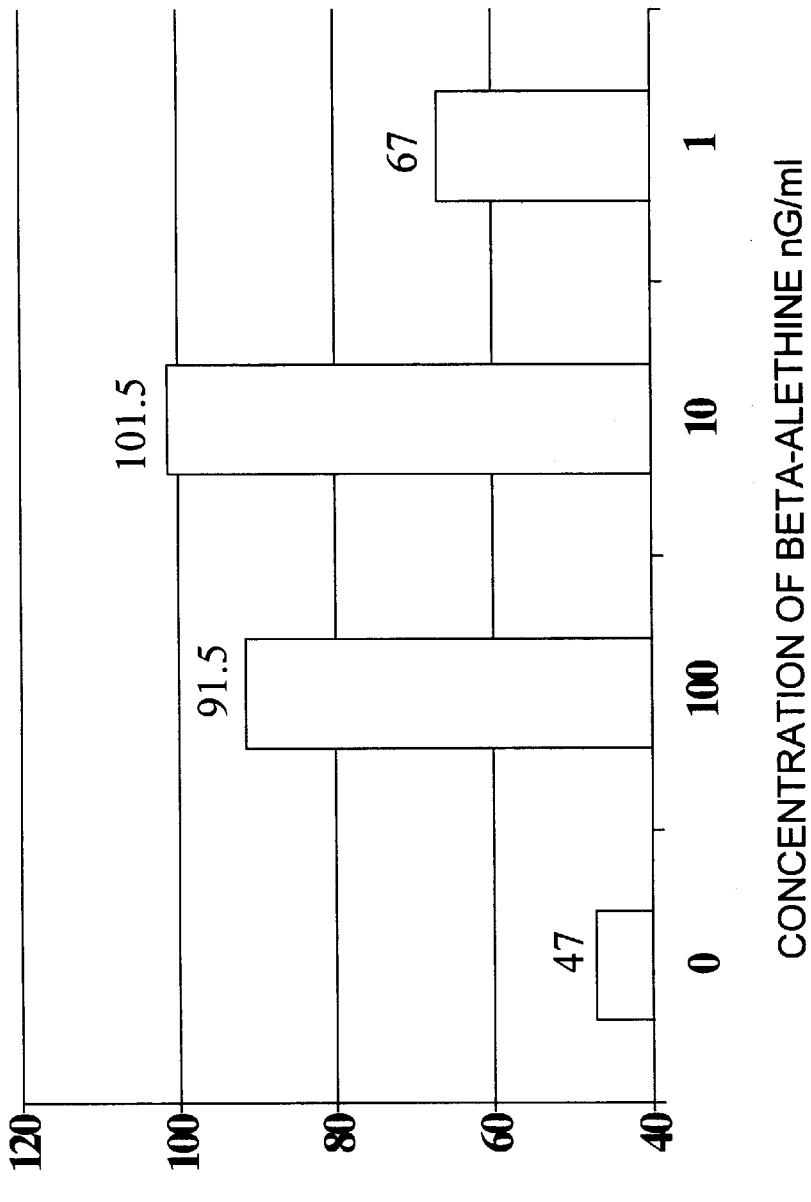
FIG. 1 illustrates data from a series of experiments designed to test the effect of β-alethine on the maximum population doubling level (PDL) of IMR-90 human fetal lung fibroblasts.

As indicated above, β-alethine is a known compound [$(H_2NCH_2CH_2(C=O)NHCH_2CH_2S)_2$ and FIG. 1, following] commonly produced by oxidation of the corresponding monosulfide, β-alethine ($H_2NCH_2CH_2(C=O)$ $NHCH_2CH_2SH$ and FIG. II, following), which is unstable in air and aqueous solutions [The Merck Index, 9th edition (#221), Merck & Co., Rahway, N.J., U.S.A.]:

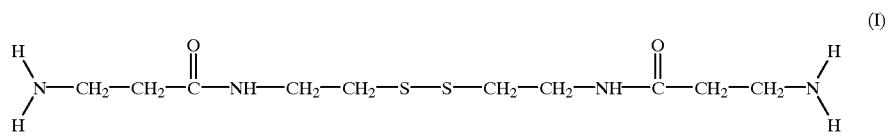

(I)

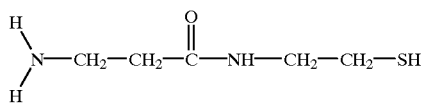

(II)

Both compounds are stabilized as their acid salts, particularly their hydrogen halide salts, and especially their hydrochloride salts. Various techniques for the synthesis of β-alethine based on deblocking of (N,N'-bis-carbobenzoxy)-blocked βalethine are described in the literature (carbobenzoxy is often abbreviated as CBZ); however, most of the known procedures result in an unsatisfactory yield purity of product, or both. Accordingly, it is preferred that β-alethine for use in the process of the invention be prepared by processes which ensure purity of product and preferably also maximize yield, for example by the process of the invention comprising coupling N-CBZ-blocked β-alanine to N-hydroxysuccinimide to produce the corresponding active ester, which is then coupled to cystamine prepared by oxidation of cysteamine with hydrogen peroxide; the product, bis-CBZ-blocked β-alethine, is then recovered and deblocked. The process is described in detail in the Examples, and provides a high-yield, high-purity product suitable for pharmaceutical use.

According to the invention, β-alethine appears to regulate a set of generic differentiation mechanisms that are not cell-lineage specific and that are common to cells regardless of phenotypic specialization. Consistent with this premise, the use of β-alethine according to the invention is not significantly dosage-dependent with respect to cell lineage, phenotype, or point of intervention in the cell cycle, except as noted below. Broadly, dosages starting from about approximately 10 pg/ml culture are useful for cellular differentiation. For in vivo applications, from about 10 pg/kg of body weight are recommended, particularly amounts from about 10 pg/kg up to about 200 μg/kg, and more particularly, up to about 100 μg/kg, which may be administered by any customary route in the presence of conventional carriers (such as physiological saline for non-oral routes including parenteral, or with suitable enterocoating in oral routes) preferably on a daily of alternate-daily regimen as described more fully below, until the desired results are achieved, although other regimens, such as weekly or biweekly regimens may suffice, particularly when results are apparent; i.e., decreases in dosages as normalization progresses may be suitable. Use of amounts of β-alethine substantially in excess of those required to obtain differentiation, normalization of cell function, or other results noted herein are not recommended, as excessive dosages may be counterproductive or at least ineffective. For in vitro applications, dosages starting from about 10 pg/ml culture are suggested, with replenishment as described below.

It is contemplated that β-alethine is useful for the differentiation of cells of living organisms in general, including mammalian (especially human), reptilian, avian, plant, insect, arachnid, rickettsial, bacterial, yeast, mold, protozoan, and fungus cells, owing to the commonality of results obtained with corresponding dosages observed in both experiments reported herein and unreported experiments and the ubiquitous presence of precursors to β-alethine in living systems. Further, β-alethine is useful for adapting to culture cells which are generally not regarded as so adaptable (herein referred to as culture-resistant cells), such as hepatic cells.

According to the invention, β-alethine comprises a differentiation compound which normalizes cell function (i.e., increases insufficient function, or decreases excess function); promotes cell longevity and/or bioproductivity; and/or diversifies cell function (i.e, expands phenotypic cellular expression). β-alethine specifically functions to (1) adapt resistant cells to culture; (2) delay senescence of cells in vitro, wherein senescence is broadly defined as the cell's increasing inability to reproduce itself in culture, typically characterized by markedly increasing cell generation times ($T_g$) at specific population doubling levels (PDL); or the time required for one complete round of cell division (see, e.g., Hayflick, R., Exp. Cell. Res. 37: 614–636 (1965), incorporated herein by reference, for a discussion of markers of senescence including $T_g$ and PDL); and (3) normalize or improve function, such as immunological surveillance (the recognition and elimination of intractable cells), and/or production of cells, especially those of the immune system (immunocytes). Particularly for delay of senescence in cell cultures, it is preferable to expose cells to be treated to β-alethine prior to significant cell malfunction (in this case, onset of senescence), as it has been found difficult, for example, to reverse cellular senescence once it has begun; thus treatment with β-alethine according to the invention includes prevention of cellular differentiative malfunction as described herein, as well as therapeutic treatment of existing differentiative malfunction, such as that associated with various diseases or disorders. Markers of abnormal cellular differentiative function denoting incipient diseases or disorders, including markers of approaching cellular senescence, are well-known or developing in the art, and practitioners are referred to the literature for methods for assessing such markers.

In order to normalize the life cycle of cells in culture, i.e., optimize growth and maturation of cells with respect to senescence and death, and adapt resistant cells to culture, it is preferred that the cells be exposed to β-alethine before the onset of senescence. Since cellular aging is a gradual procedure, senescence may to some degree be arrested even if the cells are exposed to the compound at a later stage in the life of the cells, depending upon the particular cell type, culture conditions and other factors. However, senescent cells are less viable and productive by definition, so maintaining them at this late stage of the lifespan is counterproductive for most aspects of the invention, unless, for example, study of senescent cells is of concern. Consequently, for optimum results in most instances (e.g., when optimization of cell life and function is desired) it is preferable to expose cells to the compound as early in their life-cycle as is convenient.

Culture-resistant cells (i.e., cells which have a brief lifespan under conventional culture conditions, for example of two weeks or less; or those which do not express normal biofunctions in culture, such as those wherein normal production of hormones, enzymes, or other bioproducts is suppressed in vitro) are adaptable to culture by early exposure to adaptive amounts of the compound, preferably by combining the compound with the culture medium before introducing the cells. Exemplary resistant cells include lymphoid, hepatic, pancreatic, neural, thyroid, and thymus mammalian cells.

β-alethine may be added to any known culture medium, optionally supplemented with protein components such as serum, e.g., fetal or new-born calf serum, to obtain the results of the invention; the media employed do not form a part of this invention. Exemplary media include Eagle's Basal Medium; Eagle's Minimal Essential Medium; Dulbecco's Modified Eagle's Medium; Ham's Media, e.g. F10 Medium or F12 Medium; Puck's N15 Medium; Puck's N16 Medium; Waymoth's MB 5421 Medium; McCoy's 5A Medium; RPMI Media 1603, 1534, and 1640; Leibovitz's L15 Medium; ATCC (American Type Culture Collection) CRCM 30; MCDB Media 101, 102., 103, 104; CMRL Media 1066, 1415;. and Hank's or Earl's Balanced Salt Solution. The basal medium employed, as known in the art, contains nutrients essential for supporting growth of the cell under culture, commonly including essential amino acids, fatty acids, and carbohydrates. The media typically include additional essential ingredients such as vitamins, cofactors, trace elements, and salts in assimilable quantities. Other factors which promote the growth and maintenance of cells, including compounds and factors necessary for the survival, function, production, and/or proliferation of the cells, such as hormones, for example peptidyl or steroidal hormones, growth factors, and antibiotics are also typically included. The media also generally include buffers, pH adjusters, pH indicators and the like.

Media containing the modulators of the invention are applicable to a variety of cells, especially eukaryotic cells. The media of the invention are suitable for culturing animal, especially mammalian cells including human cells; plant cells, insect cells; microorganisms such as bacteria, fungi, molds, protozoa, and rickettsia, especially antibiotic-producing cells. β-alethine is broadly useful for promoting viability of living cells in a broad spectrum of so-called tissue culture media adapted for the culture of such cells. Exemplary applications include the culture of cloned cells, such as hybridoma cell lines; of cells, mammalian cells in particular and especially human cells, for the production of cell products, particularly proteins and peptides such as hormones, enzymes, and immunofactors; of virally-infected cells for the production of vaccines; of plant cells in, for example, meristem or callus culture; of epithelial cells to provide tissue for wound healing; of resistant cells for medical and diagnostic use; and in media adapted for the production and preservation of biological organs and implant tissue.

Specific cell types useful for culture in the processes of the invention accordingly include: cells derived from mammalian tissues, organs, and glands such as the brain, heart, lung, stomach, intestines, thyroid, adrenal, thymus, parathyroid, testes, liver, kidney, bladder, spleen, pancreas, gall bladder, ovaries, uterus, prostate, and skin; reproductive cells (sperm and ova); lymph nodes, bone, cartilage, and interstitial cells; blood cells including immunocytes, cytophages such as macrophages, lymphocytes, leukocytes, erythrocytes, and platelets. Additional cell types include stem, leaf, pollen, and ovarian cells of plants; microorganisms and viruses as described above; and cells derived from insect tissues, organs, and glands.

Culture techniques useful in conjunction with the modulators of the invention include the use of solid supports, (especially for anchorage-dependent cells in, for example, monolayer or suspension culture) such as glass, carbon, cellulose, hollow fiber membranes, suspendable particulate membranes, and solid substrate forms, such as agarose gels, wherein the compound is caged within the bead, trapped with the matrix, or covalently attached, i.e. as a mixed disulfide. β-alethine is useful in primary cultures; serial cultures; subcultures; preservation of cultures, such as frozen or dried cultures; and encapsulated cells; cultures also may be transferred from conventional media to media containing the compound by known transfer techniques.

According to the practice of this one aspect of the invention, cells are treated with β-alethine in an amount effective to promote culture of these cells in vitro, as measured, for example, by significant increase in cell viability or lifespan, increase in cell biomass, or increase in cell bioproductivity, as compared to untreated cells. For in vitro applications, from about 10 pg/ml of cell culture (based on a density of from about $10^5$ to about $10^7$ cells/ml) are suggested. The culture should be replenished with the compound as necessary, generally on a daily basis; again, treatment on an alternate-day or biweekly basis may suffice, depending upon the desired results.

In immunological applications, immunocytes are exposed to β-alethine to promote and/or diversify the function of immunocytes such as leukocytes, lymphocytes, splenocytes, T-cells, B-cells, natural killer (NK) cells, and cytophages such as macrophages. In particular, β-alethine is useful in vivo or in vitro to diversify or improve splenocyte or antibody systems; to diversify or improve immunoglobulin production; to generally promote normal immunofunction of immunocytes; and to treat diseases or disorders, especially those of the immune system, by treating the organism, mammals in particular and especially humans, with effective dosages of β-alethine (optionally including an agent that promotes the growth and maintenance of cells described above) either directly, or by removing the affected cells, treating them in vitro, and reinjecting them into the affected organism. Human diseases contemplated to respond to these therapies include autoimmune diseases, hypogammaglobulinemia, and AIDS (acquired immune deficiency syndrome).

EXAMPLES

I. Preparation of β-alethine

β-alethine was produced by deblocking N,N'-bis-carbobenzoxy (CBZ) blocked β-alethine produced as follows:

A. Preparation of N,N'-bis-(CBZ)-β-alethine or 5,5-Bis [N-carbobenzoxy-β-alanyl)-2-aminoethyl]disulfide A solution of dicyclohexylcarbodiimide (23.3 g) was added to a solution of N-CBZ-β-alanine (24.84 g) and N-hydroxysuccinimide (12.92 g) in a total volume of about 500 ml of dry 10% acetonitrile in dichloromethane. Dicyclohexylurea (24.51 g) precipitated as a by-product upon formation of the active ester. The active ester was dried to an oil and triturated with anhydrous ethyl ether. The precipitate was resuspended in dichloromethane and additional dicyclohexylurea was allowed to precipitate. The resulting dichloromethane solution of active ester was filtered and added to a previously prepared solution of cystamine (8.5 g). The desired product, N,N'-bis-(CBZ)-β-alethine precipitated from this mixture. The mother liquor, anhydrous ether, dichloromethane extracts of the product, and the anhydrous ether extract of the active ester recovered above were dried and recombined to augment the yield of product. The product was substantially insoluble in water, hot (above about 70° C.) ethyl acetate, and hot (above about 30° C.) ether, and these can be used to further extract impurities. The product can also be recrystallized from dimethyl sulfoxide with acetonitrile or water, and again rinsed with ethyl acetate and ether. The later process results in a 1° C. increase in product melting point, from 180 to 181° C. (uncorrected). Yields of N,N'-bis-(CBZ)-β-alethine of up to theoretical yields are contemplated; yields of 85–90% of theory have been routinely obtained. When dried over $P_2O_5$, in vacuo, the product appears to retain one mole equivalent of water, and was analyzed accordingly as the monohydrate.

Anal. Calcd. for $C_{26}H_{34}N_4O_6S_2 \cdot H_2O$: C, 53.78; H, 6.25; N, 9.65.

Found: C, 54.23; H, 6.56; N, 9.66. Sample analyzed by Ruby Ju, Department of Chemistry, University of New Mexico, Albuquerque, N. Mex.

B. Deblocking of CBZ-blocked β-alethine obtained from I.A., above [preparation of β-alethine. 2HCl; or N,N'-bis-(β-alanyl)-cystamine; or N,N'-bis-(β-alanyl-2-aminoethyl) disulfide]

recrystallization of the β-alethine HCl from water with acetonitrile resulted in fine needles which melted at 224–225° C. (uncorrected).

Anal. Calcd. for $C_{10}H_{22}N_4O_2S_2 \cdot 2HCl$: C, 32.69; H, 6.59; N, 15.25.

Found: C, 32.52; H, 6.69; N, 15.32. Sample analyzed by Ruby Ju, Dept. of Chemistry, University of New Mexico, Albuquerque, N. Mex.

C. Characterization of β-alethine: [$^{13}C$]-NMR; [$^{1}H$]-NMR; and IR spectra of β-alethine.

| | a<br>S—$CH_2$ | b<br>$CH_2$—N | c<br>H—N—C=O | d<br>O—C—$CH_2$ | e<br>$CH_2$—N | f<br>\N—H / H + H |
|---|---|---|---|---|---|---|
| | | | [$^{13}C$]—NMR | | | |
| β-alethine | 37.59 | 39.04 | 172.79 | 32.9 | 36.71 | ----- |
| | | | [$^{1}H$]—NMR | | | |
| β-alethine | 2.524 | 3.094 | ----- | 2.694 | 3.367 | ----- |
| | | | | | | H—N—C=O \ O—R |
| bis-(CBZ)-<br>-β-alethine<br>(DMSO) | 2.740 | 3.309 | 8.085 | 2.254 | 3.192 | 7.24 |
| | a | b | c | d | e | f |
| | | | IR (cm$^{-1}$) | | | |
| | a | b | c | d | e | f |
| | | | | | | \N—H / H + H |
| β-alethine | 660w | | 3250w<br>1555w–s<br>1286m<br>1620s | ---- | | 3270v<br>2970s–w<br>1462s<br>1620s<br>1128s |
| | | | | | | H—N—C=O \ O—R |
| bis-(CBZ)-<br>-β-alethine | ---- | | 3345s<br>1545m<br>1640s | ---- | | 3345s<br>1535s<br>1270m<br>1682s |
| | a | b | c | d | e | f |

( R is a benzyl moiety in this table.)

Complete removal of the carbobenzoxy group was accomplished according to procedures described in *J. Am. Chem. Soc.* 86: 1202–1206 (1964), incorporated herein by reference. After deblocking with four equivalents of hydrogen bromide in glacial acetic acid per mole of the N,N'-bis-(CBZ)-1-alethine for 15 hours, the β-alethine was purified by precipitation with acetonitrile, rinsing with anhydrous ethyl ether, resuspension in water and filtering, and precipitating the mixed salt product with acetonitrile. Initial yields were in excess of 80% of theoretical maximum yields. β-alethine was converted to the hydrochloride salt by passing the preparation over a 30 ml×15 cm long column of Dowex AG 1×8 (chloride form) (Dow Chemical Corp., Midland, Mich., U.S.A.) which had been previously prepared by eluting with 1M KCl and rinsing thoroughly with DI (deionized) water. Neutralization with $Ca(OH)_2$ and β-alethine is unusual in that changes in pH [neutralization with $Ca(OH)_2$] cause pronounced shifts in the positions and intensities IR bands.

Peaks (HCl salt): 3270s, 3170s, 2970s, 2700w, 2550w, 2020w, 1657s, 1595m, 1560s, 1450s, 1409m, 1390w, 1354w, 1325m, 1300w, shoulder/1252m/shoulder, 1188m, 1129m, 1097m, 1079w, 1030w, 950w, 905w, 829m.

Peaks (neutralized) 3250w, 3180w, 2940m/broad, 2375s, 2230s, 2157s, 1936w, 1620s, 1555w, 1462s, 1432 shoulder, 1400m, 1342m, 1286m, 1217m, 1188m, 1128s, 1020m, 810w, 719m, 660w.

Bis-(CBZ)-β-alethine displays only a few of the resonances present in β-alethine.

Peaks: 3345s, 3310s, 1682s, 1640s, 1545m shoulder, 1535s, 1450w, 1427w, 1375w, 1332m, 1270m, 1231m, 1178w, 1120w, 1030m/broad.

II. Delay of Cellular Senescence of Fibroblasts with β-alethine.

FIG. 1 shows data from a series of experiments designed to test the effect of β-alethine on the maximum population doubling level (PDL) of IMR-90 human fetal lung fibroblasts. This cell line is available from the American Type Culture Collection (ATCC, Bethesda, Md., U.S.A.) and is used as a standard for in vitro cellular senescence studies. Cellular senescence is loosely defined as those cellular process(es) that together result in the cell's inability to replenish itself in culture. This model represents aging processes in vivo, and cell lines developed from humans of different ages have PDL's in vitro which are inversely related to the chronological age of the donor. The IMR-90 cells depicted in FIG. 1 were grown under ideal conditions in McCoy's 5A synthetic medium supplemented with HEPES buffer at 10 mM; 100 units penicillin G/ml and 100 μg streptomycin/ml at standard concentrations; new born calf serum (NBCS) at 20% (V/V); and L-glutamine at 2 mM. The treated cell cultures were augmented with different concentrations of β-alethine (as indicated) dissolved in phosphate-buffered saline (PBS)—always in a standard volume of 30 microliters per culture. The β-alethine was added to the cultures at PDL 35 which is considered Phase II or midlife of these cells in chronological terms, at the time the cells were passaged. The culture process comprised removing the adherent cells from their substrate by treating the cells with 0.25% trypsin/EDTA (ethylenediamine tetraacetic acid) solution for two to five minutes. The cells were then washed twice with the complete medium and counted in a double Neubauer hemacytometer; 2 million cells were aliquoted into a fresh tissue culture flask (T-75, polystyrene by LUX, Flow General, McClean, Md., U.S.A.) with 20 ml of fresh complete medium. This process was repeated every 48 to 72 hours when the cells reached approximately 80% surface confluency. Thus the cells were maintained under conditions which facilitate logarithmic growth, i.e., between 30 and 80% surface confluency. Under these conditions IMR-90 cells senesce at approximately PDL 45–47 (first bar on graph). Cells treated with β-alethine continued to grow well beyond this point and finally senesced in a dose-dependent manner from PDL 67 to PDL 101.5. During the β-alethine-dependent growth extension the cells were observed to have phenotypes similar to Phase II fibroblasts. At the point of eventual senescence their phenotype was similar to that of the PDL 47 untreated control. The augmentation of growth represented a doubling of the life expectancy of the cells and in absolute terms represented an increase in cell number (biomass) by a factor of 2 raised to the power 55, or $3.6 \times 10^{16}$ fold. It was concluded that this was a differentiative phenomenon, based in part on the observation that the treated cells have similar generation times (the time required for one complete round of division) before and after treatment with β-alethine, beyond the normal senescence point.

III. Differentiation of a Peripheral Lymphoid Organ With β-alethine

Figure 2:
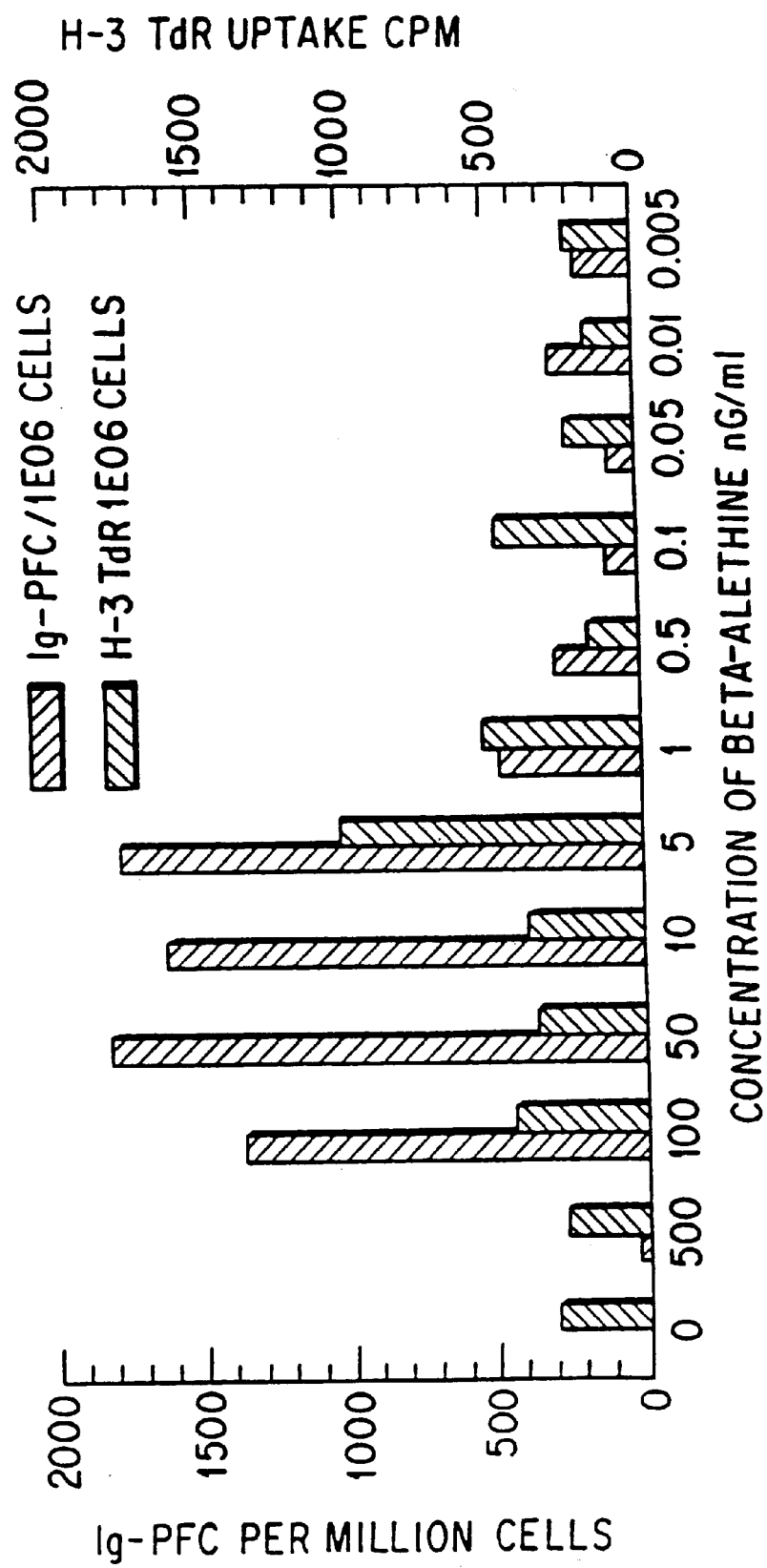
FIG. 2 illustrates data from a series of experiments designed to study the effect of β-alethine on non-antigen specific immunoglobulin synthesis and secretion by human peripheral blood leukocytes (HPBLs) in vitro.
Figure 3:
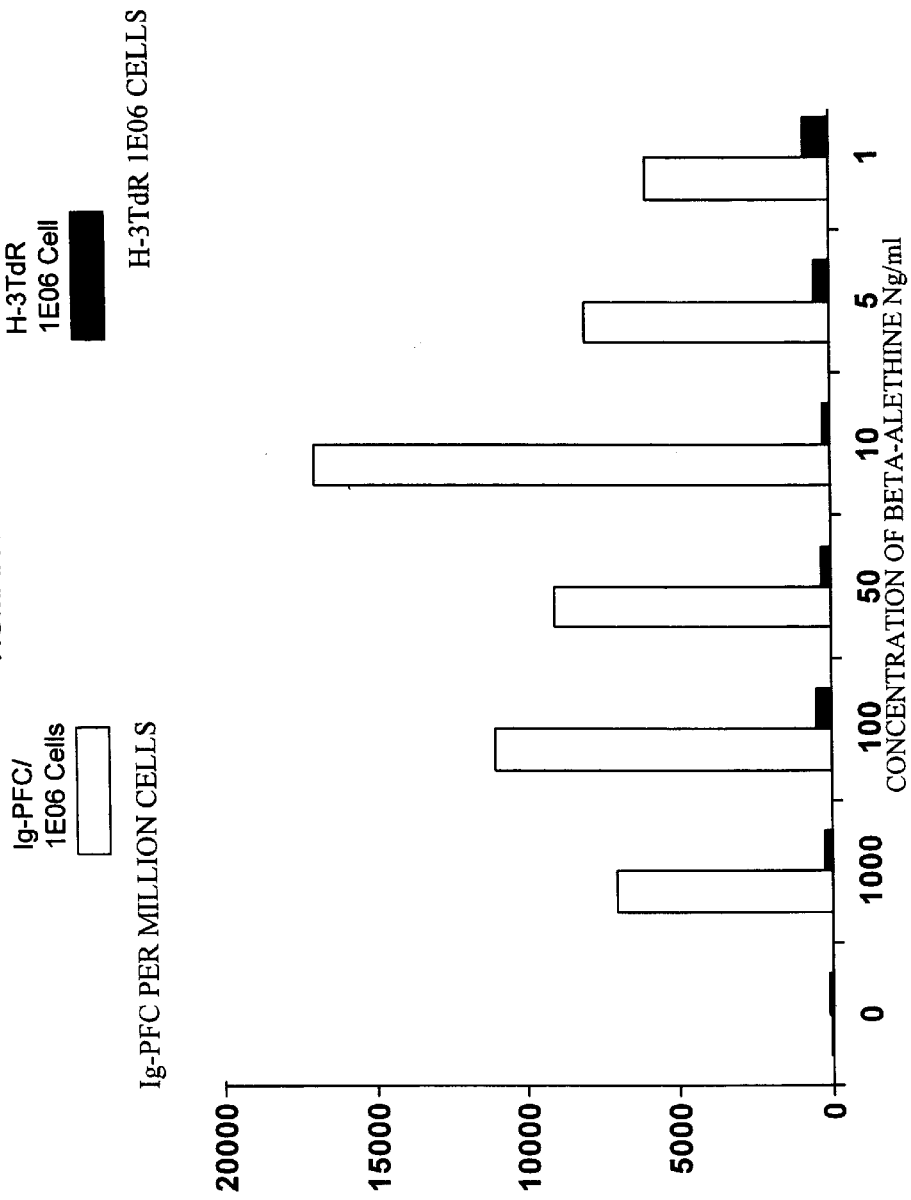
FIG. 3 illustrates data from a series of experiments designed to study the effect of β-alethine on murine splenocyte production of non-specific immunoglobulin.

FIG. 2 illustrates data from a series of experiments designed to assess the effect of β-alethine on non-antigen-specific immunoglobulin synthesis and secretion in vitro by human peripheral blood leukocytes (HPBLs), generally characterized as a peripheral lymphoid organ primarily populated by medium-sized, mature lymphocytes. In these experiments, blood was taken from healthy male humans; the blood was then defibrinated on glass beads, and the leukocytes separated by centrifugation (buffy coat technique). Residual red blood cells were lysed with a brief treatment with 0.85% ammonium chloride. The leukocytes were counted and dispensed into 24 well tissue culture trays (LUX, Flow General, McClean, Md., U.S.A.) in 1 ml of RPMI 1640 basal medium supplemented with penicillin, streptomycin, 10% fetal calf serum, and L-glutamine. β-alethine was added to test cultures at various concentrations in 30 microliter doses. The cells were harvested as indicated in FIG. 2 at various times between 72 and 144 hours of culture and tested for antibody production using a conventional protein-A facilitated plaque assay (A-PFC or Ig-PFC). In this assay, protein-A was covalently conjugated to washed sheep red blood cells (SRBC's) using chromium chloride in saline (6 mg/100 ml) and used as target in the plaque assay. In addition, aliquots of cells were also tested for proliferation status by treating them with 0.5 μCi of tritiated thymidine (6–9 Ci/mole) followed by assessing the level of incorporation of radioactivity into newly synthesized DNA. FIG. 2 shows that β-alethine stimulated the HPBLs to produce immunoglobulin in a dose-dependent manner at approximately 60 times the untreated control levels. The optimal concentration was about 5 nanograms/ml culture. The proliferation index indicated a low level of increased thymidine incorporation at 5 ng/ml doses. This 2- to 3-fold increase over background has minor significance as compared to truly proliferative stimulants such as LPS (lipopolysaccharide) of PHA (phytohemagglutinin), which under similar conditions result in the incorporation of about 200,000 cpm of radioactivity, approximately 100- to 200-fold that of control levels. It was concluded that the level of proliferation observed in the experiment was attributable to differentiation-dependent proliferation rather than to independent proliferative processes stimulated by β-alethine, or to an increase in both the survival of cells and the retentive capacity for deoxyribonucleic acids associated with viable cells.

Figure 4:
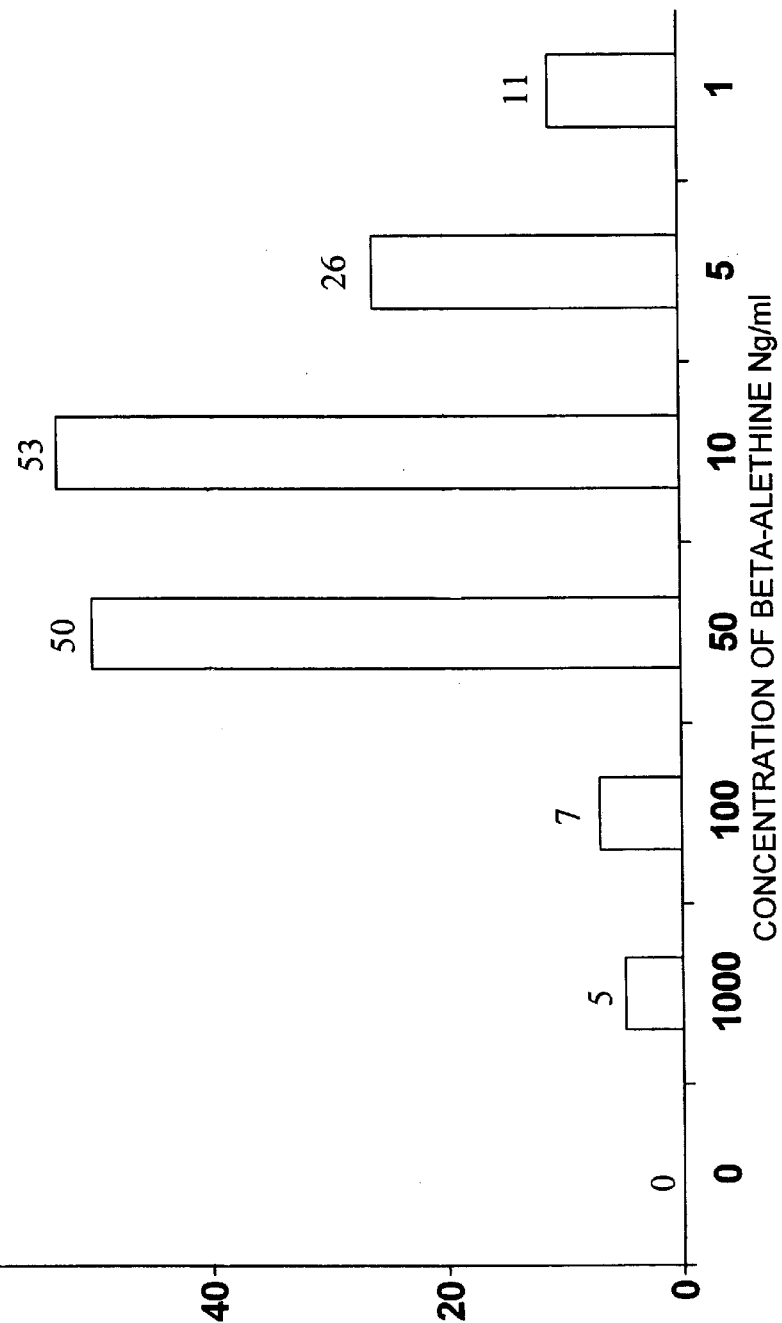
FIG. 4 illustrates data from an experiment designed to study the effect of β-alethine on the ability to adapt cells taken from in vivo or in vitro growth.
Figure 5:
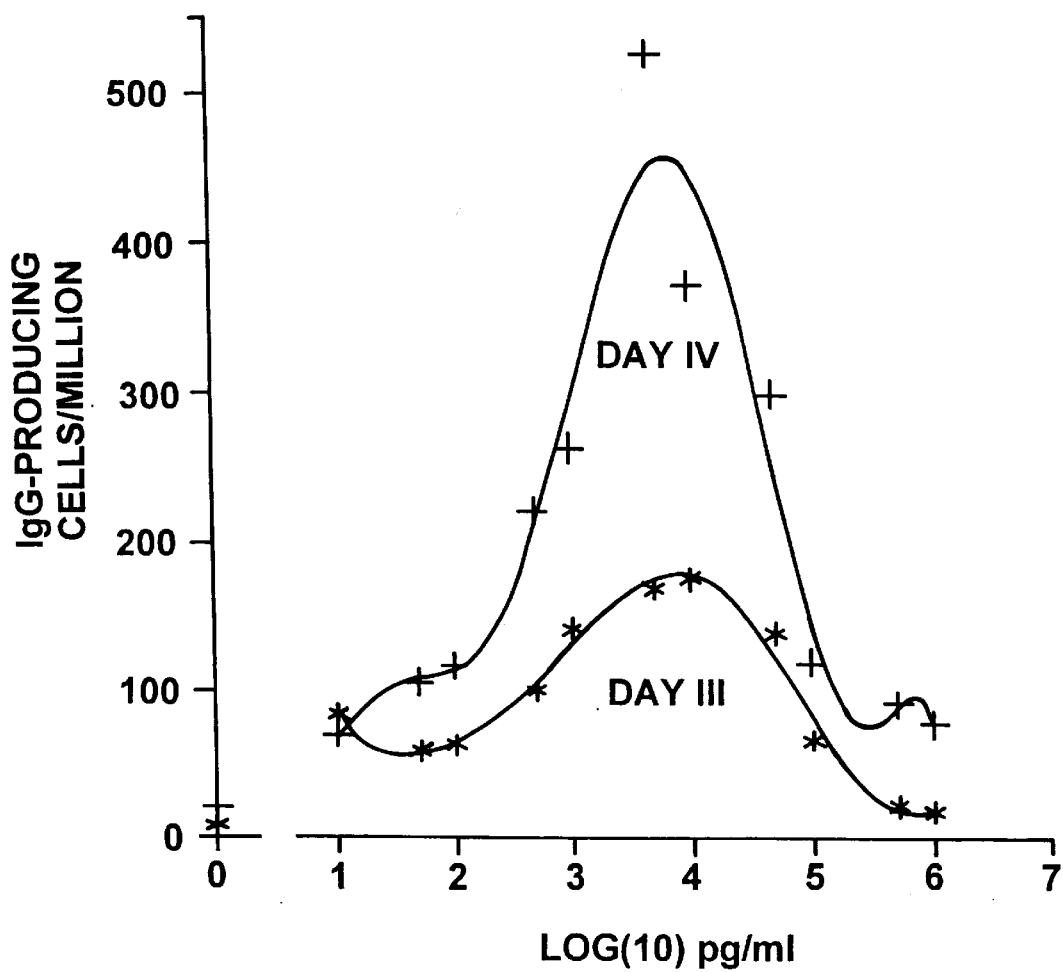
FIG. 5 illustrates data from a series of experiments designed to study the effect of β-alethine on murine splenocyte IgG production.

V. Adaptation of Culture-Resistant Cells (Hepatocytes) to Culture with β-alethine FIG. 4 illustrates data from a single experiment designed to study the use of β-alethine for adapting cells to culture. The culture-resistant cells employed (hepatocytes) were taken from in vivo to in vitro growth. Murine hepatocytes were chosen owing to their being especially difficult to adapt to culture. It has been suggested that difficulty in adapting cells to culture is related to the relative degree of differentiation of the selected cells, i.e., the more highly the cells are differentiated, the more difficult it is to culture them; accordingly, the hepatocyte mixed population of cell types were selected for this experiment on the basis that these cells are highly differentiated. In this experiment a single liver lobe from one of the BALBc/J mice was excised, pressed through a 90 mesh stainless steel screen, washed, and placed in T-25 tissue culture flasks (10 for LUX, Flow General, McClean, Md., U.S.A.). All cultures were maintained in 10 ml of the same medium as described in Example III (RPMI-1640 plus fetal calf serum plus pen/strep plus L-glutamine) and the test cultures exposed to various concentrations of β-alethine as indicated in FIG. 4. FIG. 4 shows that no colonies of hepatocytes were found in the control culture, while approximately 50 colonies were observed in cultures treated with 10 ng/ml of β-alethine. It was possible to obtain some viable colonies from the control cultures, but only if 10- to 20-fold higher initial cell concentrations were used; therefore the β-alethine was between 500- and 1000-fold more efficient in adapting murine hepatocytes to in vitro culture than control, i.e., saline-treated medium. In addition, the β-alethine-treated cells were stable in culture, in contrast to the controlled cells which are notoriously unstable in long-term culture. The effect is again dose-dependent, as illustrated.

VI. Inoculation of Mice with NS-1 Myeloma Cells

NS-1 myeloma cells (ATCC TIB 18, P3/NS1/1-Ag4-1) were employed as inoculant; these cells have proven to be about 90% effective in establishing myelomas in mice according to the exemplified procedure, and the untreated myelomas are substantially fatal within about two weeks.

The cells were grown for several passages (preferably one week) in a sterile environment consisting of RPMI 1640 (Whittaker M.A. Bioproducts, Walkersville, Md., U.S.A.) containing 10% fetal calf serum (Hyclone Laboratories, Logan, Utah, U.S.A.), 2 mM L-glutamine, 5,000 units of penicillin, and 5 mg streptomycin in 75 $cm^2$ polystyrene tissue-culture flasks (Corning Glassworks, Corning, N.Y., U.S.A.) in a humidified chamber at 37° C. and under 6% $CO_2$. To assure NS-1 propagation in vivo it is essential to remove DMSO (the cryostatic agent dimethyl sulfoxide) through several medium changes and dilutions; this also serves to maintain the cells in log-phases growth. Female BALBc/J mice were injected i.p. with $10^4$ cells in 0.1 ml of standard phosphate-buffered saline as soon as possible after weaning, transport, and indexing, as it has been found that the NS-1 cell line employed does not generally perform optimally in animals which are mature or which have equilibrated with their environment. The mice were maintained with Wayne RODENT BLOX (a rodent diet) (Wayne Research Animal Diets, Chicago, Ill., U.S.A.) ad lib. and tap water.

VII. Treatment of Inoculated Mice (Example VI) With β-alethine (Early Intervention)

A. concentrations of β-alethine as obtained above (Example I) of 1 ng/kg, 1 pg/kg, 10 μg/kg and 100 μg/kg (based on the body weight of the inoculated mice) were injected i.p. in 0.1 ml physiological saline starting the second day after tumor inoculation (day 2), and continuing every Monday, Wednesday, and Friday through day 47. This regimen was predicated on the observation that enzymes thought responsive to these compounds and which may play a role in the reported results are induced 48 hours after chemical stimulation. The inoculated mice were compared to a) untreated controls and b) to carrier-injected (saline-injected) controls.

Figure 6:
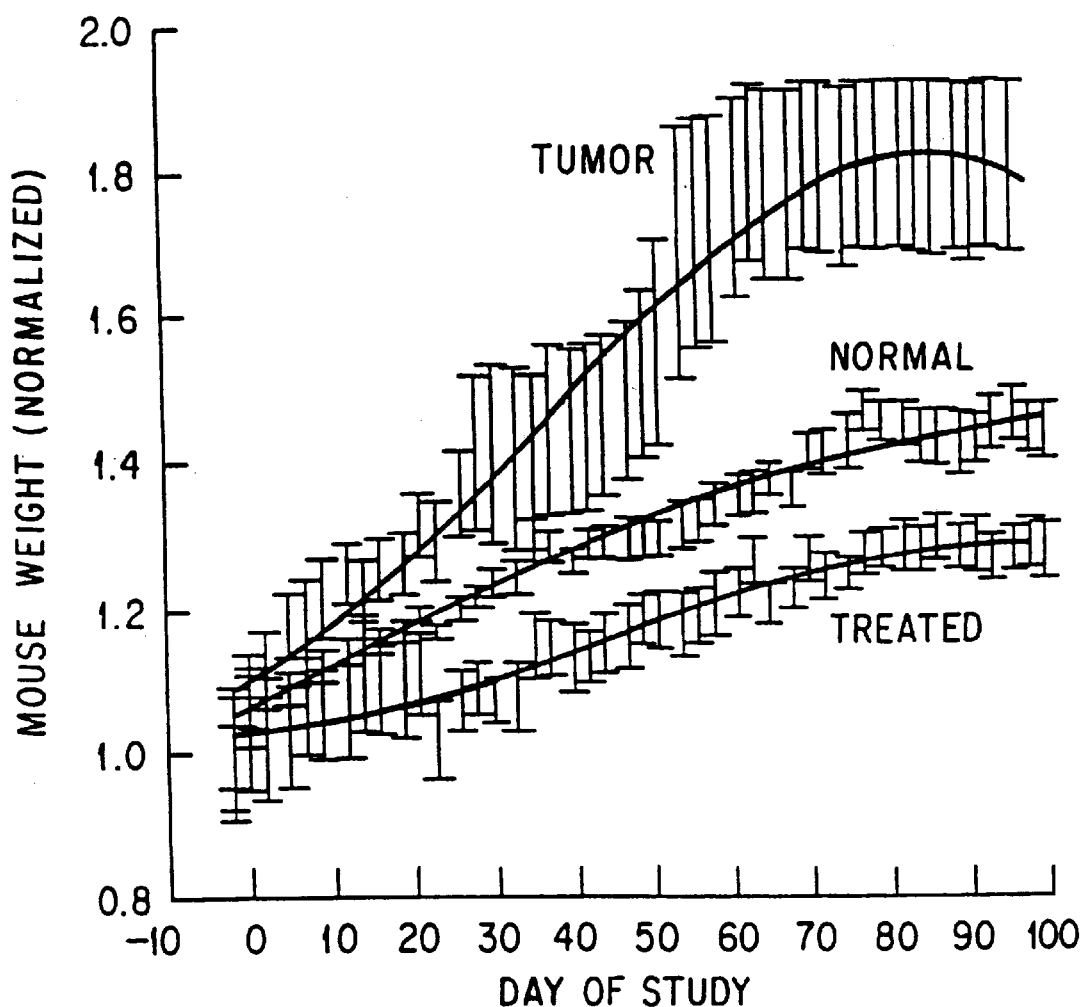
FIGS. 6–8 illustrate data demonstrating the effect of β-alethine at varying dosages on mice inoculated with NS-1 myeloma cells.
Figure 7:
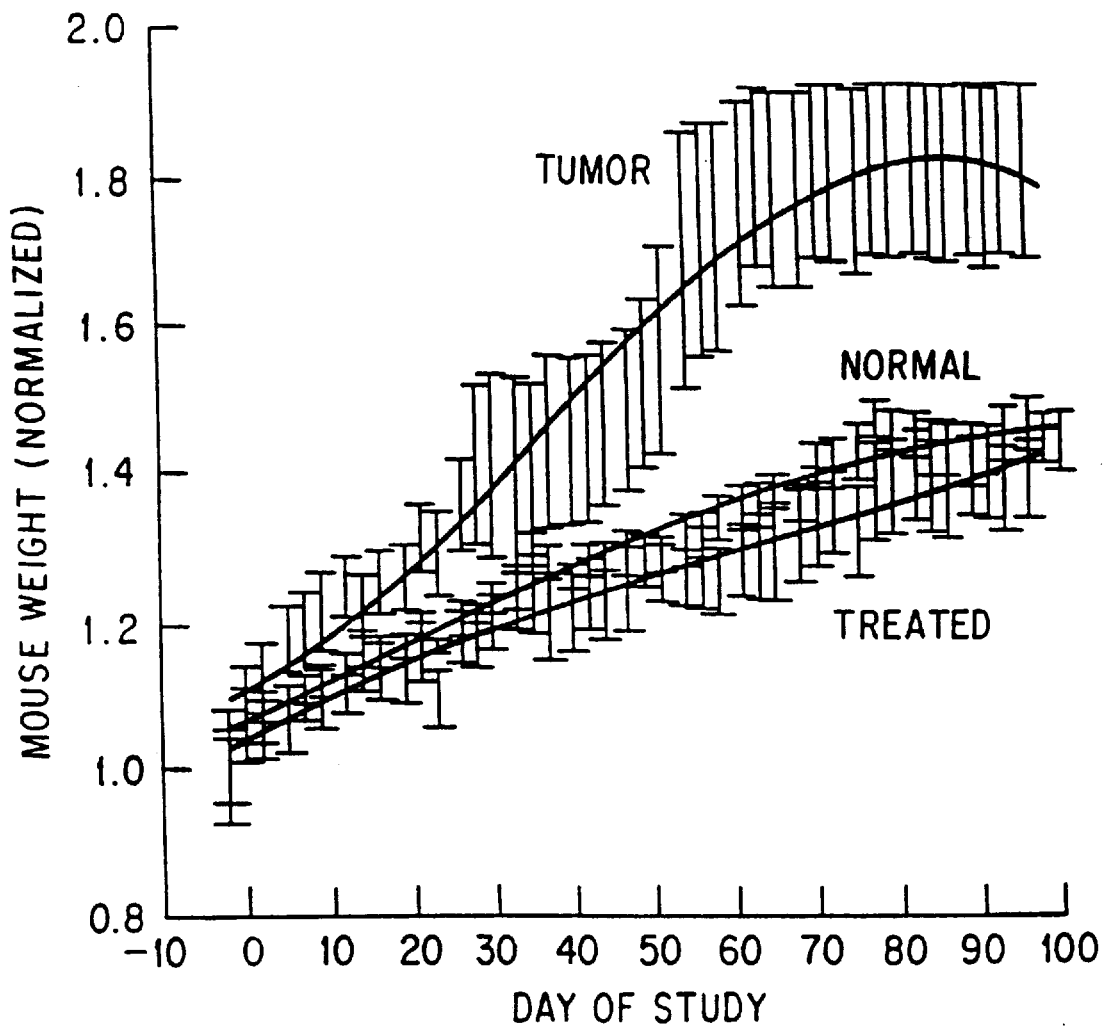
Figure 8:
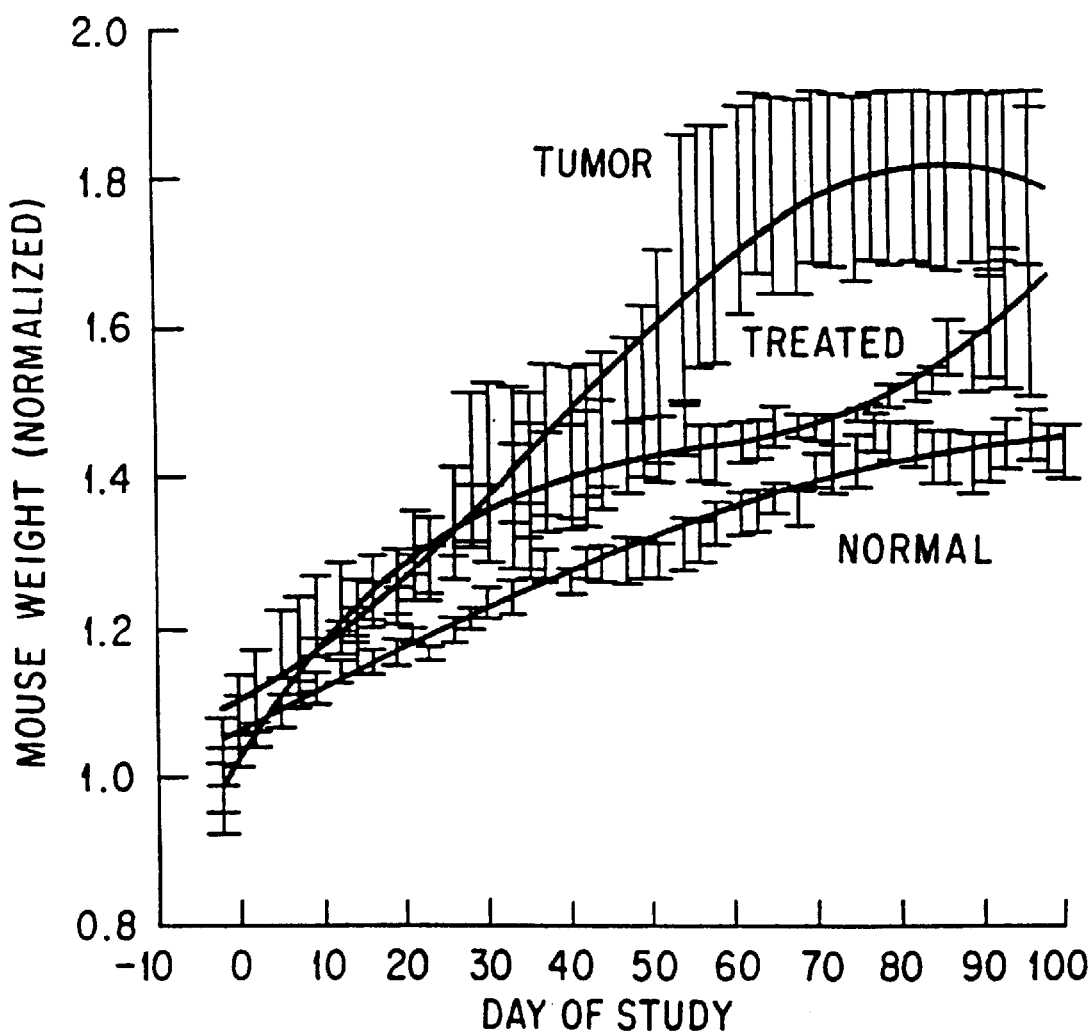

B. Conclusions

β-alethine is effective for preventing the onset of NS-1 myeloma in BALBc/J mice over the concentration range from 10 pg β-alethine/kg mouse to 100 μg/kg mouse. Without treatment, 75% of the mice in the experiment either had to be euthanized or died as the result of tumor development. At doses of β-alethine below the effective threshold [i.e., below about 10 pg/kg, or at about 10 pg/kg or 1 ng/kg (data not illustrated for the latter)] one-third to two-thirds of the animals ultimately contracted tumor. At dosages approaching the maximal effective dose (i.e., above about 10 μg/kg, or at about 10 μg/kg or 100 μg/kg), only one mouse developed a palpable tumor, which persisted for 20 days but eventually regressed. FIGS. 6–8 illustrate early and late tumor development (based on weight of mouse not attributable to normal weight gain) in mice treated with decreasing concentrations of β-alethine (100 μg, 10 μg, and 10 pg per kg mouse, respectively). In FIG. 8, the biphasic curve in the center illustrates early and late tumor development in these mice and corresponds to two deaths at this dosage (10 pg/kg mouse) of β-alethine which is the therapeutic minimal threshold for this compound in this model (FIG. 6). Normal weight gain of the mice is slightly inhibited at 100 μg/kg (FIG. 6), but not significantly at 10 μg/kg (FIG. 7). At 10 μg/kg (FIG. 7) one mouse developed a palpable tumor which persisted for 20 days but eventually regressed. At effective dosages of the antineoplastic compound β-alethine (from about 10 pg/kg body weight to about 10 μg/kg body weight), there is a striking difference between the weights of the mice (reflecting tumor burden) in the untreated control group (the vehicle-injected control group), compared with the mice in the treatment group.

Figure 9:
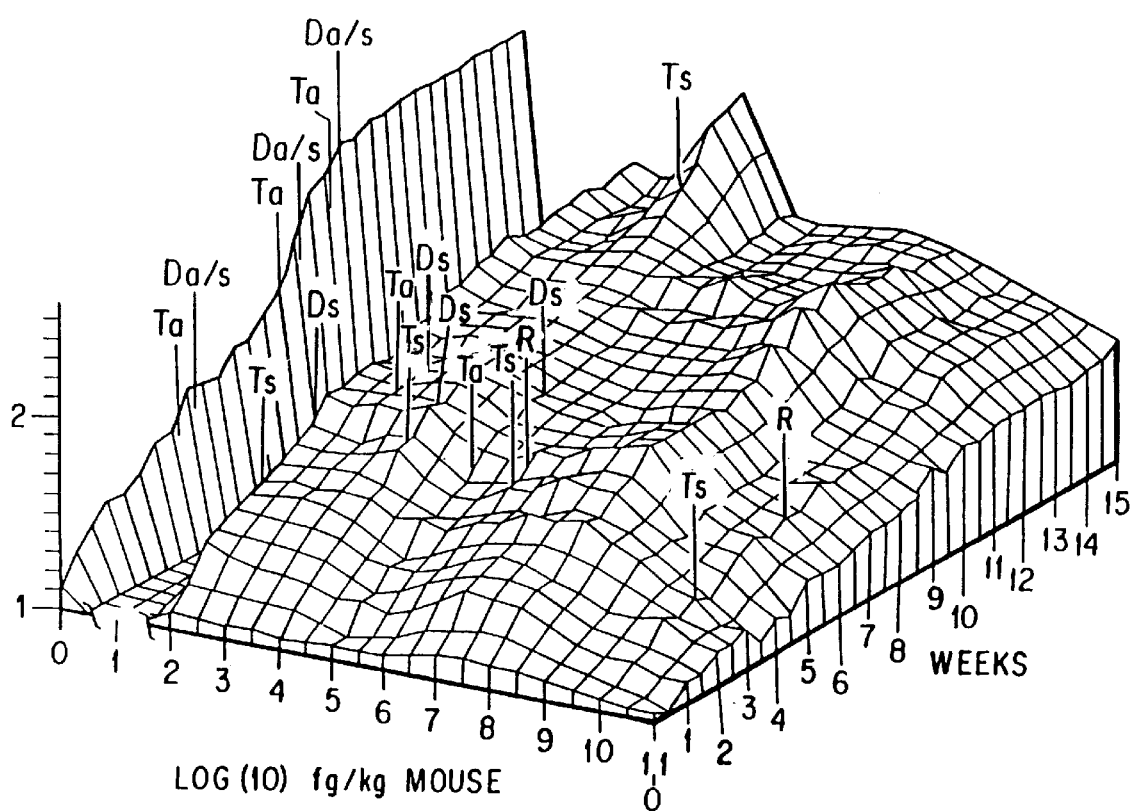
FIG. 9 is a three-dimensional composite of the data of FIGS. 6–8.
Figure 10:
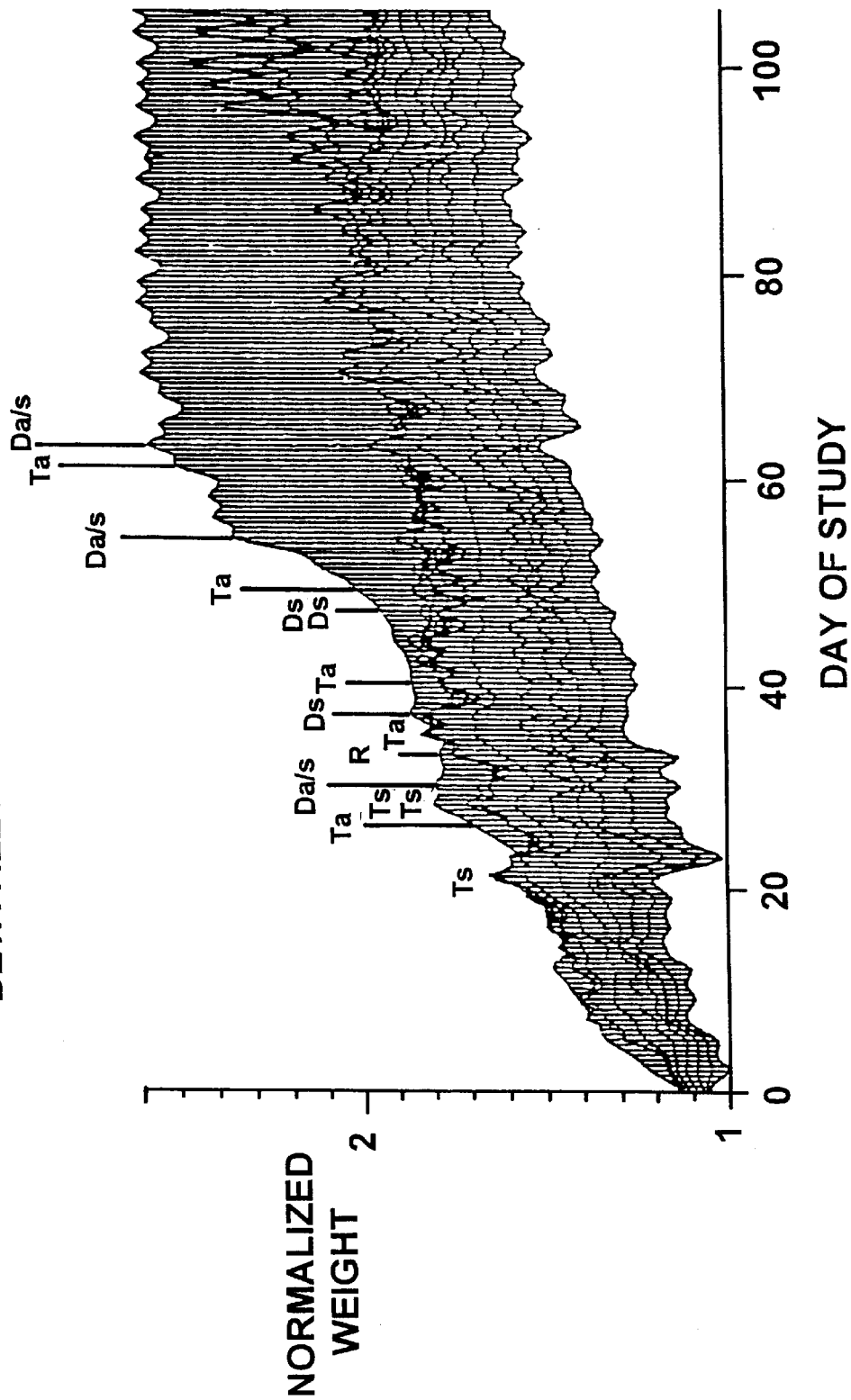
FIG. 10 is an 85° clockwise rotation of the data of FIG. 9.

The effectiveness of β-alethine in the treatment of NS-1 myeloma is further illustrated in FIG. 9, comprising a three-dimensional representation of the study; and in FIG. 10, comprising a 85° clockwise rotation of the illustration of FIG. 9, with higher doses of the drug in the front to no doses of the drug in the back. The controls inoculated with tumor (far left, FIG. 9) gain tumor and therefore weight (Z-axis) at an accelerated rate with respect to the day of the study (Y-axis). Mice receiving high doses of β-alethine (far right) develop at a near-normal rate and show no signs of chronic tumor. Ridges or increases in elevation illustrate tumor development at the lower concentrations (farther left on the X-axis) which are coded for the morphology of the developing tumor (Ta=ascites and Ts=solid tumors) and for deaths resulting from either ascites or solid tumors (Da or Ds respectively). Complete regression is indicated by R at the point at which the tumor is no longer palpable. When normalized to the initial weights of the mice in the control group and plotted (analyzed as in FIGS. 6–10), control mice (physiological saline injections only) displayed normal growth and development approximating the growth and development of the mice receiving tumor and 10 μg β-alethine/kg mouse (FIGS. 7 and 9). This is further illustrated in FIG. 10 in a mouse in which a tumor is modulated with different concentrations of β-alethine (below). The only departure from the normal growth curve coincides with the appearance and disappearance of a palpable tumor.

A tumor appeared and regressed without any signs of malaise in a mouse undergoing a therapy of 10 μg/kg β-alethine (FIG. 7). Tumors developing in untreated controls with some exceptions typically promoted ascites development, while tumors developing in mice undergoing therapy with β-alethine were with few exceptions solid masses; since it thus appears that β-alethine promotes consolidation of tumor into discrete masses, β-alethine is projected to be valuable in the design of treatment regimens involving surgical debulking.

VIII. Treatment of Inoculated Mice (Example VI) With β-alethine (Late Intervention)

Figure 11:
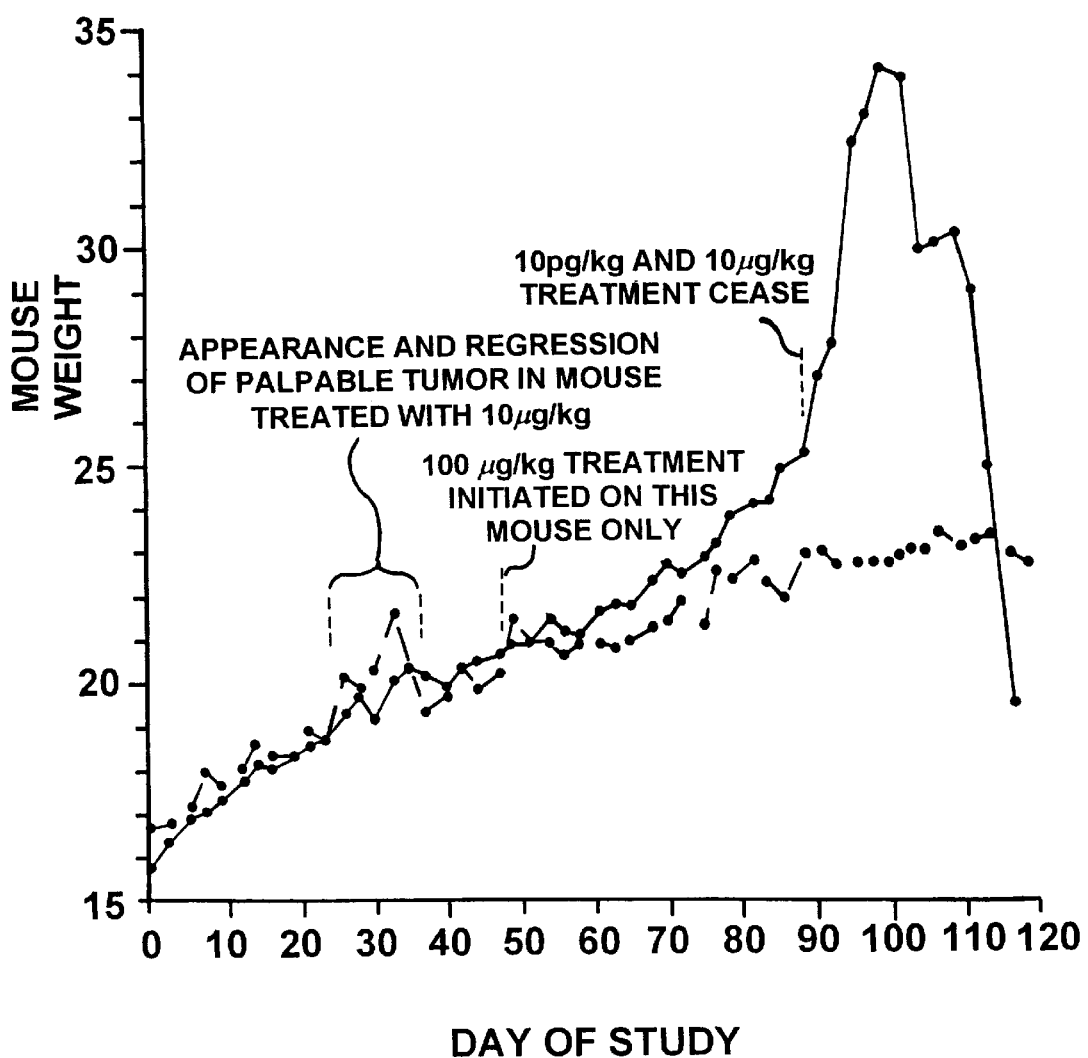
FIG. 11 illustrates modulation of tumor in a two mice each with differing amounts of β-alethine.

A single mouse developing a tumor late in the experiment (at 4 on the X-axis, FIG. 9, approximately 40 days after the 10 pg β-alethine/kg mouse treatment was discontinued) was treated with 100 μg β-alethine/kg mouse to determine the effect of late therapeutic intervention on the treatment of the myeloma (FIG. 11). Massive log-phase growth of tumor persisted along the right side of the mouse from shoulder to hip and in the abdomen for 10 to 14 days after treatment with the higher dose was begun, indicating pronounced infiltration of the tumor into extra-peritoneal tissues, and a considerable lag phase before the treatment became effective. The growth then ceased, and was followed by rapid reduction of both the tumor mass and the tumor-dependent weight of the mouse. There was a brief period in which the malaise subsided and the mouse's rough coat improved. This coincided with a temporary stabilization (approximately 1 week) of the mouse's weight suggesting that the tumor also stabilized during this time. This was followed by another precipitous drop in the mouse's weight and obvious decrease in the tumor masses. The mouse was euthanized when the weight returned to normal even though a palpable mass remained in the abdomen. At the time the mouse was euthanized, phlebitis was evident in the extremities, possibly resulting from the processing of the tumor equivalent of roughly 10% of the body weight per day. After correcting for necrosis evident histologically, it was estimated that between 85 and 90% of the original tumor was either necrotic or resorbed at the time of euthanasia. Considering the rate of resorption, there would have been complete regression of the tumor if the therapy had been maintained for the full month.

Wasting of the tumor and not the mouse proper was confirmed by weighing the debulked carcass. In this mouse, unlike untreated controls, there was no gross evidence of infiltration of organs by the tumor, and the remaining tumor appeared necrotic (yellowish-green and granular like an old sponge). Histological examination of the tissues indicated remaining tumor cells in the skeletal muscle adjacent to the abdominal wall, the subcutaneous tissue, and a mammary gland. Hepatic, Urogenital, and gastrointestinal tumors, as well as a variety of other tumors, have been consistently observed in untreated mice, indicating the highly invasive and metastatic nature of the NS-1 cell line; however, in the treated mouse, none of the remaining organs contained tumor cells. An apparent pathological bone fracture was observed in this mouse, but no tumor cells were evident in the marrow of this bone. It was thus tentatively determined that the bone demineralized due to rapid growth of the tumor resulting in the fracture, a process which requires calcium and phosphate, and which would also explain the subsequent rapid extraskeletal deposition of calcium phosphate as the tumor was resorbed.

Based on this and other studies, it is recommended that in some instances (particularly when treating large inoperable tumors) β-alethine initial dosages of about 100 µg/kg used in late intervention therapy be gradually reduced to slow the resorptive process and permit the organism to adjust to the therapy. Gradual decreases of dosages (on an alternating 48 hour regimen) from about 100 µg/kg down to about 1 ng/kg are suggested as the tumor responds to the therapy.

What is claimed is:

1. A method for adapting cells of a mammal to culture comprising exposing the cells in a culture medium to β-alethine in an amount sufficient to adapt them to culture.

2. The method of claim 1, wherein the cells are mammalian, including human cells.

3. The method of claim 1, wherein the cells are differentiated cells.

4. The method of claim 1, wherein the cells are lymphoid or epithelial cells.

5. The method of claim 4, wherein the epithelial cells are hepatic, renal, neural or thyroid cells.

6. The method of claim 1, wherein the cells are exposed to at least about 10 pg β-alethine/ml cell culture medium on a cell density of about 1,000,000 cells/ml.

7. The method of claim 4, wherein said lymphoid cells are thymus or spleen cells.

8. The method of claim 5, wherein said cells are hepatic cells.

9. The method of claim 1, wherein said cells are interstitial, chondric or osteoid cells.

10. A method for increasing the growth of mammalian cells in culture comprising exposing the cells in a culture medium to beta-alethine in an amount sufficient to increase cell growth.

11. A method for increasing the viability of mammalian cells in culture comprising exposing the cells in a culture medium to beta-alethine in an amount sufficient to increase cell viability.

* * * * *